United States Patent [19]

Garsky

[11] 3,988,304

[45] Oct. 26, 1976

[54] CYCLIC DODECAPEPTIDE DERIVATIVES OF SOMATOSTATIN AND INTERMEDIATES THEREOF

[75] Inventor: Victor M. Garsky, Havertown, Pa.

[73] Assignee: American Home Products Corporation, New York, N.Y.

[22] Filed: Aug. 25, 1975

[21] Appl. No.: 607,303

[52] U.S. Cl. ........................ 260/78 A; 260/112.5 R; 424/177
[51] Int. Cl.² ................ C08G 69/44; C07C 103/52
[58] Field of Search ............... 260/112.5 S, 78 A; 424/177

Primary Examiner—Lewis Gotts
Assistant Examiner—Reginald J. Suyat
Attorney, Agent, or Firm—Richard K. Jackson

[57] ABSTRACT

Compounds of the formula:

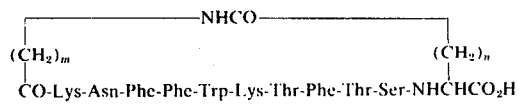

in which $m$ and $n$ are independently one of the integers from 1 to 5, inclusive, and pharmaceutically acceptable salts thereof, inhibit the release of growth hormone and are useful in the treatment of diabetes mellitus and acromegaly.

12 Claims, No Drawings

CYCLIC DODECAPEPTIDE DERIVATIVES OF SOMATOSTATIN AND INTERMEDIATES THEREOF

BACKGROUND OF THE INVENTION

This invention relates to cyclic dodecapeptide analogs of somatostatin and intermediates employed in their synthesis by a combination of the solid phase and classical method of peptide synthesis.

Somatostatin (also known as somatotropin release inhibiting factor of SRIF) is the tetradecapeptide

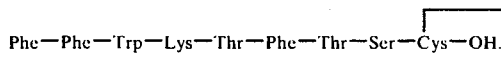

This tetradecapeptide has been identified by isolation from extracts of ovine hypothalamic tissues and found to inhibit the secretion of the hormone somatotropin which is commonly referred to as the growth hormone (GH); See Brazeau et al., Science, 179 pp 77–79 (January 1973). The linear form of this tetradecapeptide, H-Ala-Gly-Cys-Lys-Asn-Phe-Phe-Trp-Lys-Thr-Phe-Thr-Ser-Cys-OH, has also been reported by Brazeau et al., supra, to have been synthesized by solid phase methodology and found to have the same biological activity as the somatostatin obtained from a natural source.

DESCRIPTION OF THE INVENTION

In accordance with this invention there is provided a group of cyclic dodecapeptides of the formula:

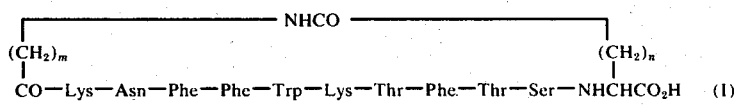

their pharmaceutically acceptable salts and intermediates employed in their production, wherein $m$ and $n$ are independently one of the integers from 1 to 5, inclusive. Each of the amino acid residues depicted in the formula, supra, which possess an assymetric carbon atom are of the L-configuration.

Illustrative of pharmaceutically acceptable acid addition salts are the hydrochloride, hydrobromide, sulfate, phosphate, maleate, acetate, citrate, benzoate, succinate, maleate, ascorbate and the like. Salts of the C-terminal amino acid moiety include the alkali metal, alkaline earth metal, ammonium, and mono-, di-, and tri (lower)alkyl amine salts.

The present invention also provides novel undecapeptide intermediates of the formula:

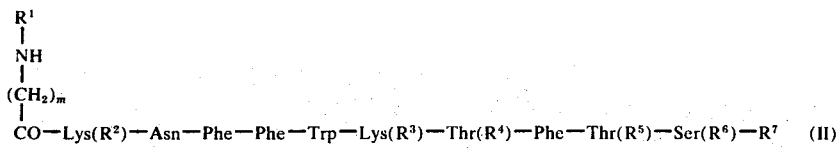

wherein:

$R^1$ is an acid labile or photolytically labile amino protecting group. It is selected for its ability to be removed without affecting the other protecting groups in the molecule, with the exception of the omega-carboxyl protective group optionally present in the C-terminal amino acid moiety ($R^8$) which, when present, is ideally removed with $R^1$.

Illustrative of suitable protecting groups defined by $R^1$ are biphenylisopropyloxycarbonyl, t-butyloxycarbonyl, trityl, t-amyloxycarbonyl, isopropyloxycarbonyl α,α-dimethyl 3,5-dimethoxybenzyloxycarbonyl, sec-butyloxycarbonyl, 3,5-dimethoxybenzyloxycarbonyl, etc. Preferably $R^1$ is t-butyloxycarbonyl;

$R^2$ and $R^3$ are protecting groups for the side chain amino substituent of lysine. Illustrative of suitable side chain amino protecting groups are benzyloxycarbonyl and substituted benzyloxycarbonyl said substituent being selected from halo (e.g., chloro, bromo, fluoro) and nitro (e.g., 2-chlorobenzyloxycarbonyl, p-nitrobenzyloxycarbonyl, 3,4-dichlorobenzyloxycarbonyl), tosyl, t-amyloxycarbonyl, t-butyloxycarbonyl, diisopropylmethoxycarbonyl; etc. The selection of such a side chain amino protecting group is critical in that it must be one which is not removed by cleavage during cleavage of the $R^1$ protecting group from the amino acid residue in the one position. Hence, the $R^1$ side chain amino protecting group cannot be the same as the $R^2$ and $R^3$ protecting groups. If $R^2$ and $R^3$ were t-butyloxycarbonyl $R^1$ would have to be a protecting group that is more acid sensitive and hence cleavable under conditions that will not cleave t-butyloxycarbonyl. Thus, $R^1$ can be biphenylisopropyloxycarbonyl;

$R^4$, $R^5$ and $R^6$ are protecting groups for the alcoholic hydroxyl group of threonine and serine and is selected from the class consisting of acetyl, benzoyl, tert-butyl, trityl, benzyl, 2,6-dichlorobenzyl and benzyloxycarbonyl. The preferred protecting group is benzyl; or $R^4$, and/or $R^5$ and/or $R^6$ is hydrogen which means there is no protecting group on the alcoholic hydroxyl function;

$R^7$ is selected from the class consisting of OH, $NHNH_2$, $N_3$, $OCH_3$ and $—O—CH_2—$[polystyrene resin support].

The group $—O—CH_2—$[polystyrene resin support] defining $R^7$ in the intermediates of this invention described supra, represents the ester moiety of one of the many functional groups of the polystyrene resin support. The resin support employed may be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky et al., Chem. Ind. (London) 38, 1597–98 (1966). A chloromethylated resin is commercially available from Bio Rad Laboratories, Richmond, Calif. and the preparation of such a resin is described by Stewart et al., "Solid Phase Peptide Synthesis" (Freeman & Co., San Francisco 1969), Chapter 1, pp 1–6.

Additional intermediate compounds of this invention are the dodecapeptides of the formula:

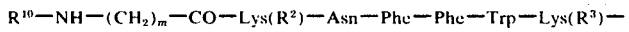
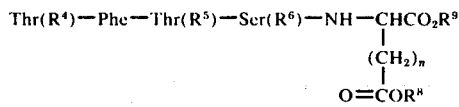

wherein:

$R^2$, $R^3$, $R^4$, $R^5$ and $R^6$ have the same meaning as set forth, supra.

$R^8$ is hydrogen or a side chain carboxyl protecting group which is removed under conditions which will not remove the $R^9$ α-carboxyl protecting group. Thus $R^8$ and $R^9$ cannot be the same protecting group. Illustrative of $R^8$ side chain carboxyl protecting groups are t-butyl and benzhydryl;

$R^9$ is an α-carboxyl protecting group. The α-carboxyl protecting group represented by $R^9$ is one which is stable under conditions which (1) remove the $R^8$ carboxyl protecting group, if one is present and (2) remove the $R^1$ side chain amino protecting group on the amino acid residue in the one position of the dodecapeptide. The $R^9$ carboxyl protecting group is illustrated by $C_1$–$C_6$ alkyl (e.g., methyl, ethyl, butyl, pentyl, isobutyl), benzyl, substituted benzyl (wherein the substituent is selected from at least one of nitro, methoxy and methyl, e.g., p-methoxybenzyl, 2,4-dimethoxybenzyl, p-nitrobenzyl, 2,4,6-trimethylbenzyl), phenacyl, phthalimidomethyl, benzhydryl, trichloroethyl, 4-picolyl, β-methylthioethyl and 4-(methylthio) phenyl. The preferred $R^9$ group is benzyl.

$R^{10}$ is selected from the class consisting of hydrogen and $R^1$.

The present invention also presents intermediates of the formula:

1476 (1973). Following the coupling of the α-amino and hydroxyl protected serine to the resin support, the α-amino protecting group is removed such as by using trifluoroacetic acid in methylene chloride, trifluoroacetic acid alone or HCl in dioxane. The deprotection is carried out at a temperature between about 0° C. and room temperature. Other standard cleaving reagents and conditions for removal of specific α-amino protecting groups may be used as described in Schroder & Lubke, supra, 1 pp. 72–75. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups illustrated by the following: formyl, trifluoroacetyl, phthalyl, toluenesulfonyl (tosyl), benzenesulfonyl, nitrophenylsulfenyl, tritylsulfenyl, o-nitrophenoxyacetyl, γ-chlorobutyryl, etc; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl, 1-(p-biphenylyl)-1-methylethoxycarbonyl, α,α-dimethyl-3,5-dimethoxybenzyloxycarbonyl and benzhydryloxycarbonyl; (3) aliphatic urethan protecting groups illustrated by tert-butyloxycarbonyl, diisopropylmethoxycarbonyl, isopropyloxycarbonyl, ethoxycarbonyl, allyloxycarbonyl; (4) cycloalkyl urethan type protecting groups illustrated by cyclopentyloxycarbonyl, adamantyloxycarbonyl, cyclohexyloxycarbonyl; (5) thio urethan type protecting groups such as phenylthiocarbonyl; (6) alkyl type protecting groups as illustrated by triphenylmethyl (trityl), benzyl; (7) trialkylsilane groups such as trimethylsilane. The preferred α-amino protecting group is tert-butyloxycarbonyl;

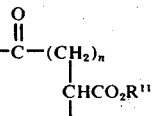
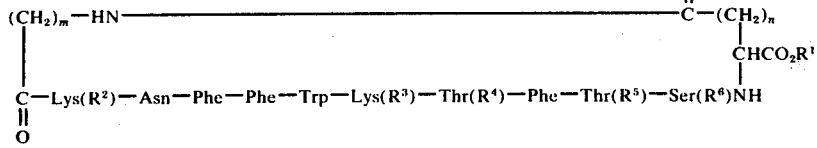

wherein:

$R^2$, $R^3$, $R^4$, $R^5$ and $R^6$ have the meaning given above, and, $R^{11}$ is a member selected from the group consisting of hydrogen and $R^9$.

The polypeptides of this invention are prepared by coupling α-amino and hydroxyl protected serine to the chloromethylated or hydroxymethylated resin according to the procedure of Gisin, Helv, Chem. Acta., 56, p.

The selection of an appropriate coupling reagent is within the skill of the art. A particularly suitable coupling reagent, is N,N'- diisopropylcarbodiimide. Other coupling agents are (1) carbodiimides (e.g., N,N'-dicyclohexylcarbodiimide, N-ethyl N'-(γ-dimethylamino propyl carbodiimide); (2) cyanamides (e.g., N,N-dibenzylcyanamide; (3) ketenimines; (4) isoxazolium salts (e.g., N-ethyl-5-phenyl isoxazolium-3'-sulfonate;

(5) monocyclic nitrogen containing heterocyclic amides of aromatic character containing one through four nitrogens in the ring such as imidazolides, pyrazolides, 1,2,4-triazolides. Specific heterocyclic amides that are useful include N,N'-carbonyldiimidazole, N,N¹-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate, isobutylchloroformate) and (8) nitrogen containing heterocyclic compounds having a hydroxy group on one ring nitrogen (e.g., N-hydroxyphthalimide, N-hydroxysuccinimide, 1-hydroxybenzotriazole). Other activating reagents and their use in peptide coupling are described by Schroder & Lubke supra, in Chapter III and by Kapoor, J. Pharm. Sci., 59, pp 1–27, (1970).

Each protected amino acid or amino acid sequence is introduced into the solid phase reactor in about a fourfold excess and the coupling is carried out in a medium of dimethylformamide: methylene chloride (1:1) or in dimethylformamide or methylene chloride alone. In cases where incomplete coupling occurs the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al., Analyt. Biochem., 34, 595 (1970).

After the desired amino acid sequence of formula II has been obtained the peptide is removed from the resin. This can be done by methanolysis to obtain a compound of the formula

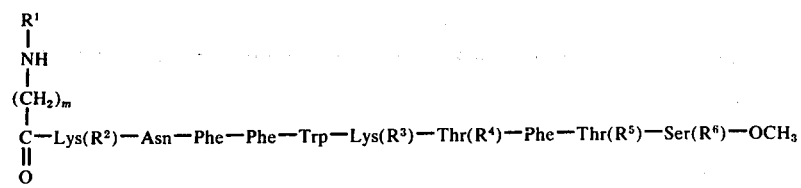

This C-terminal methyl ester is converted or directly converted to the hydrazide by reaction with hydrazine of formula II. Alternatively, hydrazine will react directly with the resin bound polypeptide to afford the hydrazide directly. The hydrazide is then converted to the corresponding azide of the formula

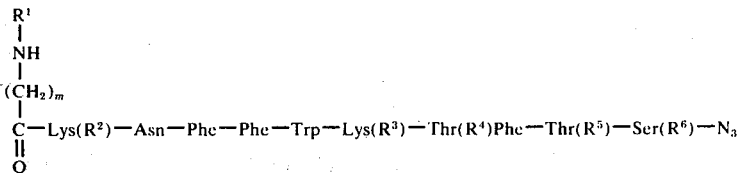

by reaction with a reagent which furnishes nitrous acid in situ. Suitable reagents for this purpose include a lower alkyl nitrite (e.g., t-butyl nitrite, isoamyl nitrite) or an alkali metal nitrite salt (e.g., sodium nitrite,, potassium nitrite) in the presence of a strong acid such as hydrochloric, phosphoric, sulfonic, etc. This reaction is carried out in the presence of either water and/or a non-aqueous solvent such as dimethylformamide, tetrahydrofuran, dioxane, chloroform, methylene chloride, etc., at a temperature between about −40° and +20° C. The azide, preferably not isolated from the reaction medium, is then coupled with an amino acid of the formula

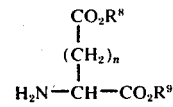

wherein $n$ is an integer from 1 through 5 inclusive, to obtain a dodecapeptide of the formula:

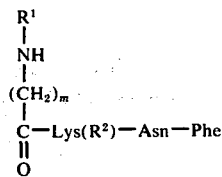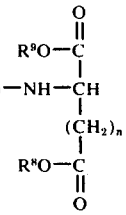

This coupling is carried out between a temperature of about −50° and +50° C., preferably between about −25° and +10° C.

The dodecapeptide is then reacted with a cleaving reagent that will split off both the side chain amino protecting group $R^1$ on the amino acid residue in one position as well as the $R^8$ carboxyl protecting group, if one is present, to yield a compound of the formula

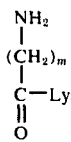
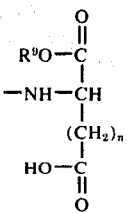

This cleavage can also be effected selectively, if desired, to first remove either the $R^1$ or $R^8$ protecting group, followed by cleavage of the other protecting group. It is essential that the cleaving reagent be one which does not remove $R^2$, $R^3$ or $R^9$ at this stage of the synthesis. A particularly suitable cleaving reagent is trifluoroacetic acid where $R^1$ is t-butyloxycarbonyl, $R^2$ and $R^3$ are 2-chlorobenzyloxycarbonyl, $R^8$ is t-butyl and $R^9$ is benzyl. The selection of other compatible reagents for removal of the $R^1$ side chain amino protecting group without cleavage of the $R^2$ and $R^3$ protecting groups is described by Schroder & Lubke, supra, 1 pp 72–75, the disclosure of which is incorporated herein by reference. While it is preferred that the side chain protecting groups represented by $R^4$, $R^5$ and $R^6$ not be split off at this stage, such groups can be cleaved, if desired so as to obtain a compound of the formula chloroform, dioxane, tetrahydrofuran and mixtures thereof. Other cyclization reagents may also be used as exemplified by the coupling reagents described, supra, as well as those described by Kopple, J. Pharm. Science, 61 pp. 1345–1356 (1972) the disclosure of which is incorporated herein by reference.

A compound of formula I is then produced by cleaving the $R^2$ and $R^3$ side chain amino protecting groups, the $R^9$ $\alpha$-carboxyl protecting group along with any protecting groups represented by $R^4$, $R^5$ and $R^6$. Suitable cleaving systems are hydrogen over a palladium catalyst or hydrogen fluoride. The cleavage step, if desired, can be carried out step wise by the selection of a reagent that will only cleave the $R^9$ $\alpha$-carboxyl protecting group, followed by use of a reagent that will cleave any other side chain protecting groups. The selection of suitable cleaving reagents that are compatible with the particular side chain and $\alpha$-carboxyl pro-

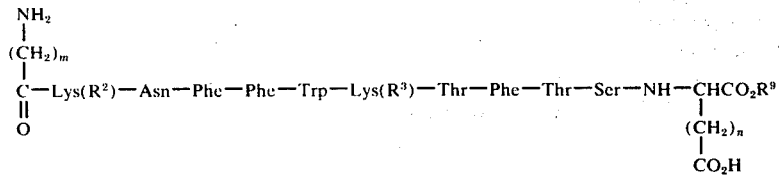

In either event, the dodecapeptide is then cyclized to produce a compound of the formula tecting groups that can be used are described by Schroeder and Lubke, supra, pp 72–75.

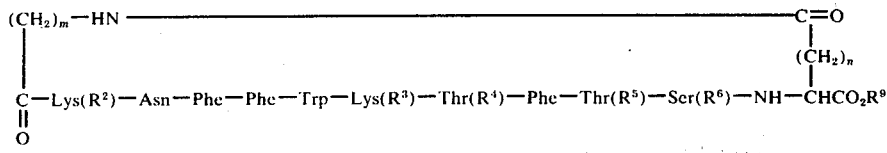

This cyclization is preferably carried out using N,N'-dicyclohexylcarbodiimide (DCC) and N-hydroxybenzotriazole in the presence of an organic solvent in a temperature range between −40° and +20° C. Suitable solvents include dimethylformamide, dichloromethane, An alternate route to preparing hydrazides and azides is to convert a compound of the formula

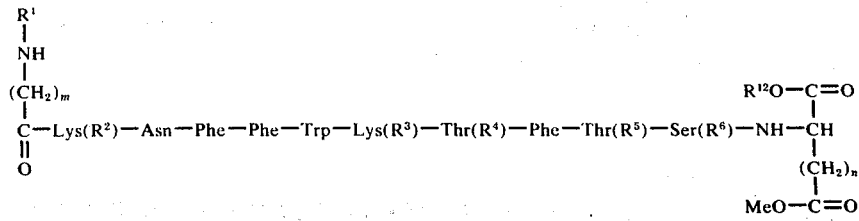

wherein $R^{12}$ is selected from the class consisting of hydrogen and $R^9$ and Me is methyl, to the corresponding hydrazide by reaction with hydrazine to obtain

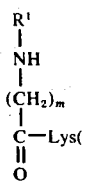
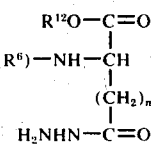

C—Lys(R²)—Asn—Phe—Phe—Trp—Lys(R³)—Thr(R⁴)—Phe—Thr(R⁵)—Ser(R⁶)—NH—CH and thereafter converting this compound to the corresponding azide by reaction with a reagent that will yield nitrous acid in situ as previously described. The azide is then cyclized after first removing the R¹ side chain amino protecting group.

The reactants employed to introduce the C-terminal amino acid group are known prior art materials and/or can be readily prepared by conventional techniques from the well known unprotected amino acids, namely aspartic acid, glutamic acid, α-aminoadipic acid, α-aminopimelic acid and α-aminosuberic acid. The preparation of these amino acids is described by Farkasova et al., Col. Czechoslov. Chem. Commun. 30, 3117 (1965); The preparation of ω-carboxyl protected esters is described by Schroder et al., Annalen 673, pp 196, 208 (1964) and Rudinger et al., Col. Czechoslov. Chem. Commun. 32, 1229 (1967).

The amino acids used in the one position of the polypeptides of this invention are either commercially available or readily prepared by prior art techniques. Thus, β-alanine, 4-aminobutanoic acid, 5-aminopentanoic acid, 6-amino hexanoic acid and 7-amino heptanoic acid are well known compounds. The amino protective group R¹ is introduced into these reactants in the conventional manner.

The following procedure exemplifies the preparation of the compounds of this invention.

EXAMPLE

Tertiary-butyloxycarbonyl-4-aminobutyryl-N$^\epsilon$ -(2-chlorobenzyloxycarbonyl)-L-lysyl-L-asparaginyll-phenylalanyl-L-phenylalanyl-L-tryptophyl-N$^\epsilon$ -(2-chlorobenzyloxycarbonyl)-L-lysyl-O-benzyl-L-threonyl-L-phenylalanyl-O-benzyl-L-threonyl-O-benzyl-L-serine methylated polystyrene resin.

Chloromethylated polystyrene resin (20.0 g., 0.75 m moles Cl/g.) is heated in a 500 ml. round bottom flask with t-butyloxycarbonyl (t-Boc)-O-benzyl-L-serine (9.2 g., 31 m moles) and potassium tertiary-butyl alcoholate (3.12 g., 28 m moles) in dimethyl sulfoxide (200 ml.), for 4 hours. The resin is filtered and washed on the filter with ethanol, methylene chloride, 15% triethylamine in methylene chloride, dimethylformamide, methylene chloride and methanol (three times each). The peptide-resin is subjected to a ninhydrin test following the procedure of E. Kaiser, et al., Analytical Chemistry 34, 595 (1970). It should be negative at this stage. The resin is at this point substituted to the extent of 0.42 m moles of t-Boc-O-benzyl-L-serine per gram of resin.

The t-Boc-O-benzyl-L-serine resin (14.0 g., 5.6 m moles) is placed in a Beckman 990 peptide synthesizer reaction vessel and treated in the following manner:

1. methylene chloride (three times)
2. 5 minute prewash with 1:1 trifluoroacetic acid-methylene chloride (v/v) containing 0.5% dithioerythritol
3. 30 minute deprotection with the above described trifluoroacetic acid
4. methylene chloride (six times)
5. 15% triethylamine in dimethylformamide (three times)
6. methylene chloride (six times)

A contact time of 1.5 minutes is allowed for each wash unless otherwise indicated.

The resin is gently stirred with t-Boc-O-benzyl-L-threonine (11.2 g., 36 m moles in methylene chloride) and 40.0 ml. of 1M diisopropylcarbodiimide (DIC) in methylene chloride (DIC added in two equal portions over 30 minutes). After stirring for 4 hours the peptide-resin is washed successively with methylene chloride, dimethylformamide and methylene chloride (three times each). To test for completeness of reaction the peptide resin is subjected to a ninhydrin test. It should be negative (or nearly so) at this stage. Any unreacted sites are acylated with acetylimidazole (70 ml., 2.5% in methylene chloride) for 30 minutes and the resin washed with methylene chloride (six times).

The deprotection of the attached amino acid is carried out as described in steps (1) through (6) above.

The following amino acid residues are then introduced consecutively: t-Boc-L-phenylalanine (9.5 g., 36 m moles in methylene chloride, 40 m moles DIC), t-Boc-O-benzyl-L-threonine (11.2 g., 36 m moles in methylene chloride, 40 m moles DIC), t-Boc-N$^\epsilon$ -(2-chlorobenzyloxycarbonyl)-L-lysine (15.0 g., 36 m moles in 50% methylene chloride-dimethylformamide, 40 m moles DIC), t-Boc-L-tryptophane (11.0 g., 36 m moles in dimethylformamide, 40 m moles DIC). The reaction time for each coupling is 4 hours unless noted otherwise. Following each coupling the peptide-resin is washed and acylated as described above. Removal of the α-amino protecting group at each step is performed as described for the deprotection of the t-Boc-L-serine-resin (steps 1–6). The washed hexapeptide-resin is dried, weighed (21.0 g.) and the synthesis continued with 50% (10.5 g., 3 m moles) of the peptide-resin. The following amino acid residues are further introduced: t-Boc-L-phenylalanine (4.75 g., 18 m moles in methylene chloride, 20 m moles DIC) t-Boc-L-phenylalanine (4.75 g., 18 m moles in methylene chloride, 20 m moles DIC), t-Boc-L-asparagine-p-nitrophenylester (6.4 g., 18 m moles in 1% acetic acid-dimethylformamide, 24 hour coupling), t-Boc-N$^\epsilon$ -(2-chlorobenzyloxycarbonyl)-L-lysine (7.45 g., 18 m moles in 50% methylene chloride-dimethylformamide, 20 m moles DIC). The decapeptide-resin is dried, weighed (12.2 g.) and the synthesis continued with 7.0 g., (1.6 m moles) of the peptide-resin. The next amino acid added is t-Boc-4-aminobutyric acid (2.8 g., 14 m moles in methylene chloride, 16 m moles DIC). After washing, the resin is dried in vacuo to yield 7.1 g.

By substituting an equivalent amount of t-Boc-β-alanine, t-Boc-5-amino pentanoic acid, t-Boc-6-amino hexanoic acid or t-Boc-7-amino heptanoic acid for the t-Boc-4-amino butyric acid, the corresponding N-terminal amino and intermediate is produced.

t-Boc-4-aminobutyryl-N$^\epsilon$ -(2-chlorobenzoyloxycarbonyl)-L-lysyl-L-asparaginyl-L-phenylalanyl-L-phenylalanyl-L-tryptophyl-N$^\epsilon$ -(2-chlorobenzyloxycarbonyl)-L-lysyl-O-benzyl-L-threonyl-L-phenylalanyl-O-benzyl-L-threonyl-O-benzyl-L-seryl-hydrazide The product of the preceding preparation (7.1 g.) is suspended in dimethylformamide (70 ml) and stirred with hydrazine (3.0 ml., 93 m moles) for 48 hours (25° C.). The resin is then filtered and washed twice with dimethylformamide. The filtrate and washes are combined and concentrated under reduced pressure maintaining a temperature of < 25° C. The resulting oil is triturated with water to yield a white precipitate. After filtration the precipitate is dried in vacuo to yield the above titled produce (2.4 g.)

t-Boc-4-aminobutyryl-N$^\epsilon$ -(2-chlorobenzyloxycarbonyl)-L-lysyl-L-asparaginyl-L-phenylalanyl-L-phenylalanyl-L-tryptophyl-N$^\epsilon$ -(2-chlorobenzyloxycarbonyl)-L-lysyl-O-benzyl-L-threonyl-L-phenylalanyl-O-benzyl-L-threonyl-O-benzyl-L-seryl-α-benzyl-β-tert-butyl-L-aspartate A solution of the product of the preceding preparation (1.05 g., 0.50 m moles) in dimethylsulfoxide (2.0 ml.) - dimethylformamide (25 ml.) is cooled to −30° C., and 1.0 N hydrochloric acid in tetrahydrofuran (1.35 ml., 1.35 m moles) added. The bath is warmed to −20° C. and t-butylnitrite (0.078 ml.) added. The solution is stirred for 30 minutes at −15° C. and to it added H-Asp-4-t-butyl-1-Bzl (0.180 g., 0.55 m moles) in dimethylformamide (3 ml.). The pH of the reaction is adjusted to ≈ 8.0 with triethylamine and the reaction stirred at −15° C. for 2 hours then a 0° C. for 1 hour and 25° C. for 18 hours. The mixture is concentrated under reduced pressure and the resulting oil triturated with citric acid (150 ml., 0.50 M). The precipitate is filtered, washed with water and dried to yield 1.14 g. of product.

By substituting 2-amino pentanedioic acid-1-benzyl-5-t-butyl-dioic ester, 2-amino hexanedioic acid-1-benzyl-6-t-butyldioic ester, 2-amino heptanedioic acid 1-benzyl-7-t-butyl-dioic ester, 2-amino octanedioc acid 1-benzyl-8-t-butyl-dioic ester for the 2-amino butanedioic acid 1-benzyl-4-t-butyl-dioic ester (H-Asp-4-t-butyl-1-Bzl), the corresponding C-terminal intermediate is produced.

4-Aminobutyryl-N$^\epsilon$ -(2-chlorobenzyloxycarbonyl)-L-lysyl-L-asparaginylL-phenylalanyl-L-phenylalanyl-L-tryptophyl-N$^\epsilon$ -(2-chlorobenzyloxycarbonyl)-L-lysyl-O-benzyl-L-threonyl-L-phenylalanyl-O-benzyl-L-threonyl-O-benzyl-L-seryl-α-benzyl-L-aspartate The protected dodecapeptide product of the preceding paragraph (1.14 g.) was treated with a 30% solution of trifluoroacetic-methylene chloride (70 cc) containing dithioerthritol (0.5%) for 40 minutes at 25° C. The solution was concentrated to an oil and triturated with anhydrous diethyl ether. A white precipitate was filtered, washed with additional diethyl ether and dried to yield 1.10 g. of product.

4-Aminobutyryl-L-lysyl-L-asparaginyl-L-phenylalanyl-L-phenylalanyl-L-tryptophyl-L-lysyl-L-threonyl-L-phenylalanyl-L-threonyl-L-seryl-L-aspartic acid cyclic (12β → 1)-peptide, diacetate The dodecapeptide of the preceeding paragraph, 4-aminobutyryl-Lys(ClCbz)-Asn-Phe-Phe-Trp-Lys(ClCbz)-Thr(Bzl)-Phe-Thr(Bzl)-Ser(Bzl)-Asp(OH)OBzl (1.1 g., 0.475 m moles) is dissolved in 300 ml. of dimethylformamide-methylene chloride (2:1). To the solution is added N-hydroxybenzotriazole (0.73 g., 10 eq.) and it is cooled in an ice bath. A solution of dicyclohexylcarbodiimide (0.78 g., 8 eq. in 10 ml. dimethylformamide) is added and the reaction stirred at 0° C. for 3 hours then at 25° C. for 72 hours. The mixture is evaporated to an oil and triturated with a solution of saturated sodium bicarbonate. After filtration the precipitate is washed thoroughly with water, 10% citric acid, water and dried. The dried solid is treated in vacuo with anhydrous liquid hydrogen fluoride (50 ml.) and anisole (5 ml.) at 0° C. for 45 minutes. The hydrogen fluoride and anisole are then removed under reduced pressure and the residue suspended in diethyl ether. After filtering, the residue is dissolved in 2 N acetic acid and lyophilyzed to leave the above titled crude product (0.85 g.).

Purification and characterization of 4-aminobutyryl-L-lysl-L-asparaginyl-L-phenylalanyl-L-phenylalanyl-L-tryptophyl-L-lysyl-L-threonyl-L-phenylalanyl-L-threonyl-L-servyl-L-aspartic acid cyclic (12β → 1)-peptide The above titled crude product is purified as follows: 0.85 g. of material is dissolved in a minimum amount of 2N acetic acid and applied to a column (2.5 × 200 cm.) of Sephadex G-25 (fine) in 2N acetic acid. The column effluent is monitored by the the Folin-Lowry color reaction on every third fraction. Fractions 140–158 are shown to be homogenous by thin laver chromatography systems 4:1:5 (n-butanol : acetic acid : water) and 7:7:6 (isoamyl alcohol : pyridine : water). Thin layer Chromatograms are visualized with iodine and chlorine peptide reagent.

R$_f$ 4:1:5 (cellulose) 0.70
R$_f$ 7:7:6 (cellulose) 0.75

After hydrolysis of the peptide in 4 N methanesulfonic acid for 18 hours (110° C.) the following amino acid analysis was obtained: Asp, 1.90; Lys, 2.00; Phe, 2.85; Trp, 0.75; Ser, 0.78; Thr, 1.94; 4-aminobutyric acid 1.04.

The reaction scheme may be generally depicted as follows:

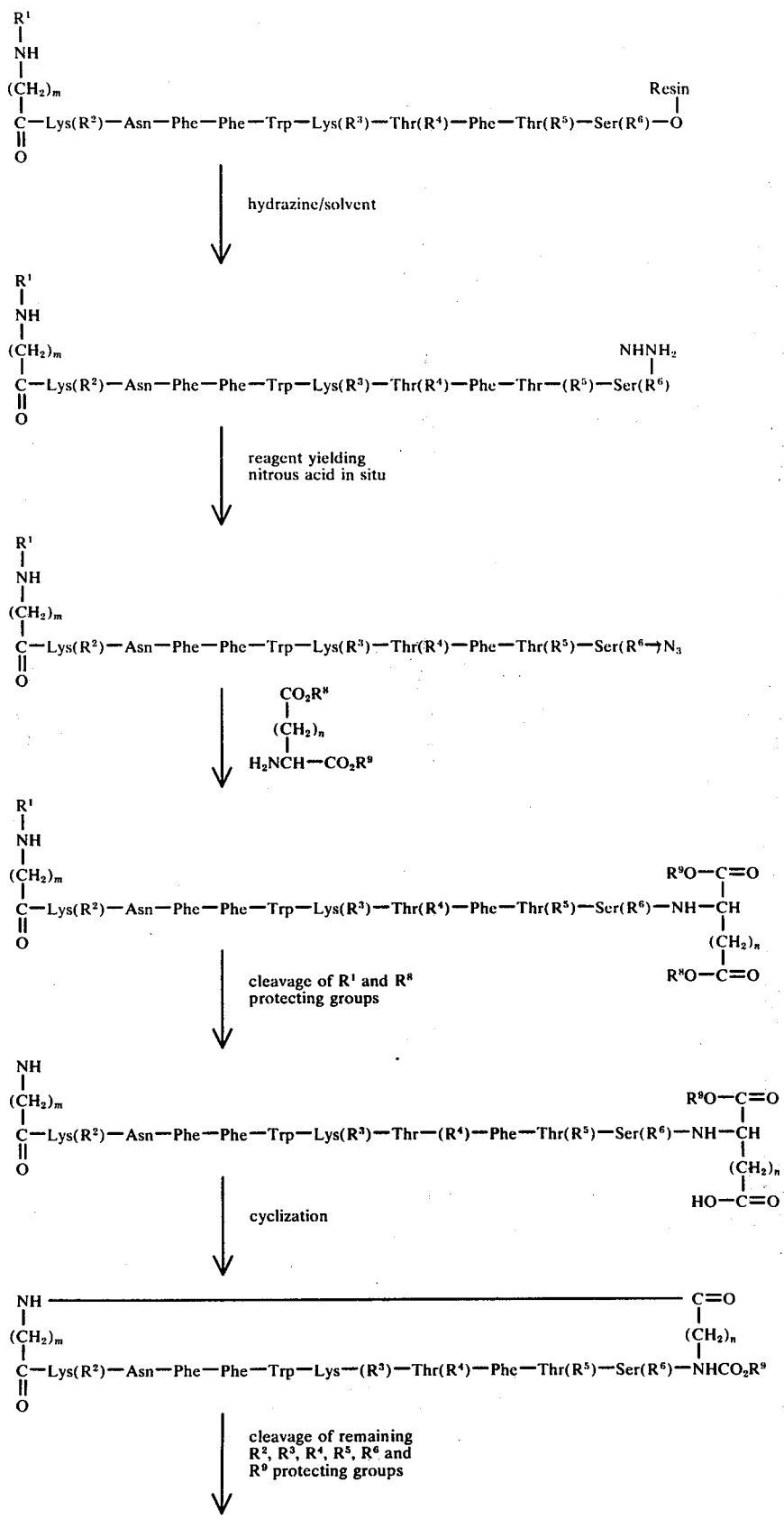
Formula I

The in vivo activity of the cyclic dodecapeptides of this invention was established with the representative test compound:

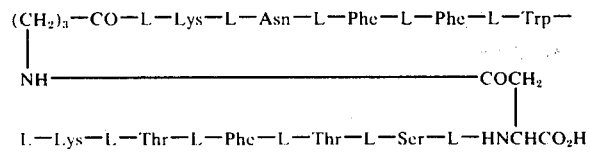

in accordance with the following test procedure:

Paired control and test Charles River CD unfasted male rats weighing from 200 – 240 grams were given Nembutal at a dose of 50 mg/kg 5 minutes before the control rats were administered vehicle subcutaneously and the test rats were administered a known quantity of the compound of the above-formula in the same vehicle subcutaneously. Fifteen minutes later, blood samples were taken by cardiac puncture and the plasma was separated for radio immunoassay of growth hormone concentration. The difference is concentration of growth hormone between the control and the paired experimental animal were evaluated by the student $t$ test at a statistical significance at the 0.05 level or lower.

At 1 milligram per kilogram, the test compound effected a decrease in blood serum growth hormone to 39± 4 nanograms per milliliter in 15 minutes while the paired control animals exhibited 169± 29 nanograms per milliliter (p<0.001) with 9 animal pairs. One hour after administration of the test compound of this invention to eight animals in another experiment, the growth hormone concentration of the blood serum was 90± 17 nanograms per milliliter while 10 control animals exhibited 213± 53 (p<0.05) nanograms per milliliter.

Following the test procedure described above, with the exception that the blood samples were taken by decapitation rather than cardiac puncture, the test compound of this invention was administered at 3 milligrams per kilogram to afford a blood analysis in 15 minutes 31 ± 3 nanograms per milliliter growth hormone; 163 ± 13 micro units per milliliter insulin; and 6.7 ± 1.4 picograms per milliliter glucagon, with 10 animals. The 10 animal control exhibited 154 ± 23 nanograms per milliliter growth hormone; 166 ± 11 micro units per milliliter insulin; and 7.7 ± 1.2 picograms per milliliter glucagon. Hence, the compounds of this invention, by analogy with the representative test compound, are effective agents in reducing blood serum growth hormone concentrations without materially changing the insulin and glucagon levels. This selective activity is especially valuable in the treatment of acromegaly and related diseases where it is desired to reduce growth hormone concentration without otherwise effecting the insulin and glucagon levels of the blood. In addition, by administration of the compounds of this invention with agents capable of reducing or increasing insulin or glucagon blood concentrations selectively, it is possible to tailor the concentration of these substances to best advantage in the treatment of the specific problem of a given patient.

The compound of formula I described herein may be administered to warm blooded mammals, including humans, either intravenously, subcutaneously, intramuscularly or orally to inhibit the release of growth hormone where the host being treated requires therapeutic treatment for growth hormone excess which is associated with diabetes mellitus and acromegaly. The contemplated dose range for oral administration in tablet or capsule form to large mammals is about 0.015 mg to about 7 mg/kg of body weight per day while the does range for intravenous injection in an aqueous solution is 0.14 µg to about 0.15 mg/kg of body weight per day. When administered subcutaneously or intramuscularly a dose range of about 1.5 µg to about 7 mg/kg of body weight per day is contemplated. Obviously, the required dosage will vary with the particular condition being treated, the severity of the condition and the duration of treatment.

If the compounds of this invention are administered in tablet form the tablet may contain: a binder such as gum tragacanth, corn starch, gelatin, an excipient such as dicalcium phosphate; a disintegrating agent such as corn starch, alginic acid, etc.; a lubricant such as magnesium stearate; and a sweetening and/or flavoring agent such as sucrose, lactose, wintergreen, etc. Suitable liquid carriers for intravenous administration include isotonic saline, phosphate buffer solutions, etc.

What is claimed is:

1. A compound selected from the group consisting of

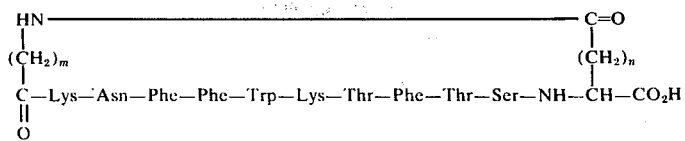

and

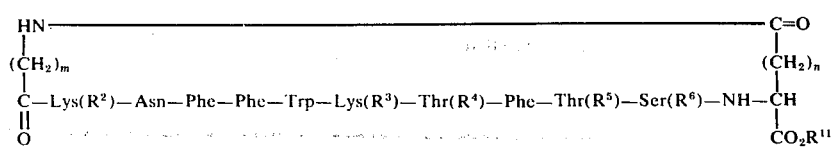

and pharmaceutically acceptable salts thereof, wherein:

$R^2$ and $R^3$ are, independently, protecting groups for the side chain amino substituent of lysine selected from benzyloxycarbonyl, tosyl, t-amyloxycarbonyl, t-butyloxycarbonyl, diisopropylmethoxycarbonyl and substituted benzyloxycarbonyl where in said substituent is selected from halo and nitro;

$R^4$, $R^5$ and $R^6$ are selected from the group consisting of hydrogen and a protecting group for the alcoholic hydroxyl group of threonine and serine selected from acetyl, benzoyl, tert-butyl, trityl, benzyl, 2,6 dichlorobenzyl and benzyloxycarbonyl;

$R^{11}$ is selected from the group consisting of hydrogen and an α-carboxyl protecting group selected from $C_1$–$C_6$ alkyl, benzyl, substituted benzyl, phenacyl, phthalimidomethyl, benzhydryl, trichloroethyl, 4-picolyl, β-methylthioethyl, 4-(methylthio)phenyl, said substituent of benzyl being selected from nitro, methyl and methoxy; and Each of $m$ and $n$ is an integer of from 1 through 5, inclusive; and all chiral amino acids are of the L-configuration.

2. A compound of claim 1 wherein $R^2$ and $R^3$ are 2-chlorobenzyloxycarbonyl, $R^4$, $R^5$ and $R^6$ are benzyl, $R^{11}$ is benzyl, $m$ is 2 and $n$ is 1.

3. A compound of the formula

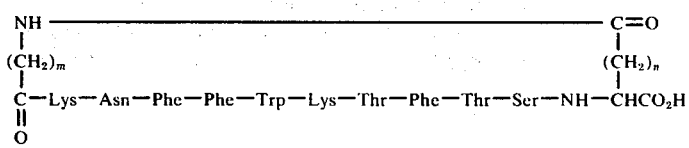

and pharmaceutically acceptable salts thereof, wherein each of $m$ and $n$ is a whole number from 1 through 5; and all chiral amino acids are in the L-configuration.

4. A compound according to claim 3 which is selected from 4-aminobutyryl-L-lysyl-L-asparaginyl-L-phenylalanyl-L-phenylalanyl-L-tryptophyl-L-lysyl-L-threonyl-L-phenylalanyl-L-threonyl-L-seryl-L aspartic acid cyclic (12β → 1) peptide and the pharmaceutically acceptable salts thereof.

5. A compound of the formula

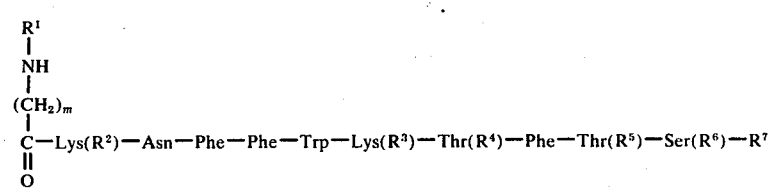

wherein:
$R^1$ is an acid labile or photolytic labile protecting group that is cleavable under conditions that will not remove the $R^2$ and $R^3$ protecting groups;

$R^2$ and $R^3$ are, independently, protecting groups for the side chain amino substituent of lysine selected from the class consisting of benzyloxycarbonyl, tosyl, t-amyloxycarbonyl, t-butyloxycarbonyl, diisopropylmethoxycarbonyl and substituted benzyloxycarbonyl, said substituent selected from halo and nitro and said $R^2$ and $R^3$ groups being stable to cleavage under conditions that result in cleavage of said $R^1$ group;

$R^4$, $R^5$ and $R^6$ are, independently, selected from the group consisting of hydrogen and a protecting group for the alcoholic hydroxyl group of threonine and serine from acetyl, benzoyl, tert-butyl, trityl, benzyl, 2,6 dichlorobenzyl and benzyloxycarbonyl; and $R^7$ is selected from the group consisting of OH, $NHNH_2$, $N_3$, $OCH_3$ and —O—$CH_2$—[polystyrene resin support];

$m$ is a whole number from 1 through 5; and all chiral amino acids in said compound are in the L-configuration.

6. A compound according to claim 5 wherein $R^1$ is t-butyloxycarbonyl, $R^2$ and $R^3$ are 2-chlorobenzyloxycarbonyl and $R^4$, $R^5$ and $R^6$ are benzyl.

7. A compound according to claim 6 wherein $R^7$ is $NHNH_2$.

8. A compound according to claim 6 wherein $R^7$ is —O—$CH_2$—[polystyrene resin support].

9. A compound selected from those of the formula

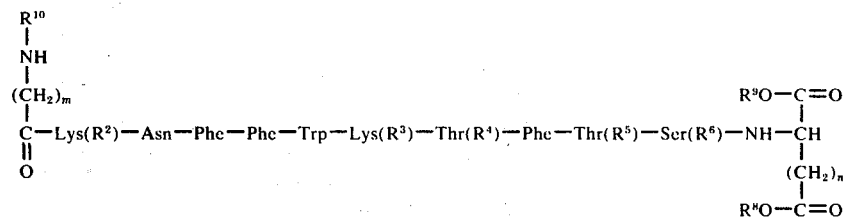

wherein:
$R^2$ and $R^3$ are protecting groups for the side chain amino substituent of lysine selected from the class consisting of benzyloxycarbonyl, tosyl, t-amyloxycarbonyl, t-butyloxycarbonyl, diisopropylmethoxycarbonyl and substituted benzyloxycarbonyl, said substituent being selected from halo and nitro, said $R^2$ and $R^3$ groups being stable to cleavage under conditions that result in cleavage of said $R^{10}$ group;

$R^4$, $R^5$ and $R^6$ are selected from the group consisting of hydrogen and a protecting group for the alcoholic hydroxyl group of threonine and serine selected from acetyl, benzoyl, tert-butyl, trityl, benzyl, 2,6-dichlorobenzyl and benzyloxycarbonyl;

$R^8$ is hydrogen or a side chain carboxyl protecting group which is removable under conditions that will not remove the $R^9$ carboxyl protecting group;

$R^9$ is an α-carboxyl protecting group which is stable under reaction conditions which cleave said $R^{10}$ and $R^8$ protecting groups, said α-carboxyl protecting group being selected from the class consisting of $C_1$–$C_6$ alkyl, benzyl, phenacyl, phthalimidomethyl, benzhydryl, trichloroethyl, 4-picolyl, β-methylthioethyl, 4-(methylthio)phenyl and substituted benzyl, said substituent being selected from the group consisting of nitro, methoxy and methyl;

$R^{10}$ is hydrogen or an acid labile or photolytic labile protecting group that is cleavable under conditions that will not remove said $R^2$ and $R^3$ protecting groups;

each of m and n is a whole number from 1 through 5; all chiral amino acids in said compounds being of the L-configuration.

10. A compound according to claim 9 wherein $R^2$ and $R^3$ are 2-chlorobenzyloxycarbonyl, $R^4$, $R^5$ and $R^6$ are benzyl, $R^8$ is t-butyl, $R^9$ is benzyl and $R^{10}$ is t-butyloxycarbonyl.

11. A compound according to claim 9, wherein $R^2$ and $R^3$ are 2-chlorobenzyloxycarbonyl, $R^4$, $R^5$ and $R^6$ are benzyl, $R^8$ is hydrogen, $R^9$ is benzyl and $R^{10}$ is hydrogen.

12. A compound of the formula

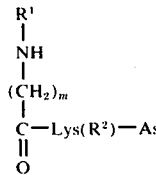 —Lys($R^2$)—Asn—Phe—Phe—Trp—Lys($R^3$)—Thr($R^4$)—Phe—Thr($R^5$)—Ser($R^6$)—NH—CH 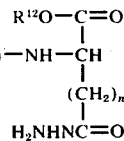

wherein $R^1$ is an acid labile or photolytic labile protecting group that is cleavable under conditions that will not remove the $R^2$ and $R^3$ protecting groups;

$R^2$ and $R^3$ are protecting groups for the side chain amino substituent of lysine selected from the class consisting of benzyloxycarbonyl, tosyl, t-amyloxycarbonyl, t-butyloxycarbonyl, diisopropylmethoxycarbonyl and substituted benzyloxycarbonyl, said substituent being selected from halo and nitro, said $R^2$ and $R^3$ groups being stable to cleavage under conditions that result in cleavage of said $R^1$ group;

$R^4$, $R^5$ and $R^6$ are selected from the group consisting of hydrogen and a protecting group for the alcoholic hydroxyl group of threonine and serine selected from acetyl, benzoyl, tert-butyl, trityl, benzyl, 2,6-dichlorobenzyl and benzyloxycarbonyl;

$R^{12}$ is selected from the class consisting of hydrogen and an α-carboxyl protecting group selected from the group consisting of $C_1$–$C_6$ alkyl, benzyl, phenacyl, phthalimidomethyl, benzhydryl, trichloroethyl, 4-picolyl, β-methylthioethyl, 4-(methylthio)phenyl and substituted benzyl, said substituent being selected from the group consisting of nitro, methoxy and methyl;

each of m and n is a whole number from 1 through 5; all chiral amino acids in said compounds being of the L-configuration.

* * * * *